United States Patent [19]

Katzer et al.

[11] 4,260,518

[45] Apr. 7, 1981

[54] PROCESS FOR THE REGENERATION OF METALLIC CATALYSTS

[75] Inventors: James R. Katzer; Hassan Windawi, both of Newark, Del.

[73] Assignee: University of Delaware, Newark, Del.

[21] Appl. No.: 39,130

[22] Filed: May 15, 1979

[51] Int. Cl.³ .................. B01J 21/20; B01J 23/94; B01J 23/96; C07C 1/04
[52] U.S. Cl. .................. 252/411 S; 252/419; 260/449 M; 260/449.6 M
[58] Field of Search .................. 252/411 S, 419, 416; 260/449 M, 449.6 M

[56] References Cited

U.S. PATENT DOCUMENTS

| | | | |
|---|---|---|---|
| 2,455,419 | 12/1948 | Johnson | 252/411 S |
| 2,609,345 | 9/1952 | Easly et al. | 252/419 |
| 3,660,308 | 3/1972 | Hayes | 252/416 |
| 4,007,131 | 2/1977 | Gillespie et al. | 252/419 |
| 4,026,821 | 5/1977 | Schoofs et al. | 252/419 |
| 4,079,072 | 3/1978 | Finch | 252/411 S |
| 4,211,718 | 7/1980 | Finch et al. | 260/449 M |

FOREIGN PATENT DOCUMENTS 1221856 2/1971 United Kingdom .

Primary Examiner—P. E. Konopka

[57] ABSTRACT

A method for the regeneration of metallic hydrogenation catalysts from the class consisting of Ni, Rh, Pd, Ir, Pt and Ru poisoned with sulfur, with or without accompanying carbon deposition, comprising subjecting the catalyst to exposure to oxygen gas in a concentration of about 1-10 ppm. intermixed with an inert gas of the group consisting of He, A, Xe, Kr, $N_2$ and air substantially free of oxygen to an extent such that the total oxygen molecule throughout is in the range of about 10 to 20 times that of the hydrogen sulfide molecular exposure producing the catalyst poisoning while maintaining the temperature in the range of about 300° to 500° C.

4 Claims, 2 Drawing Figures

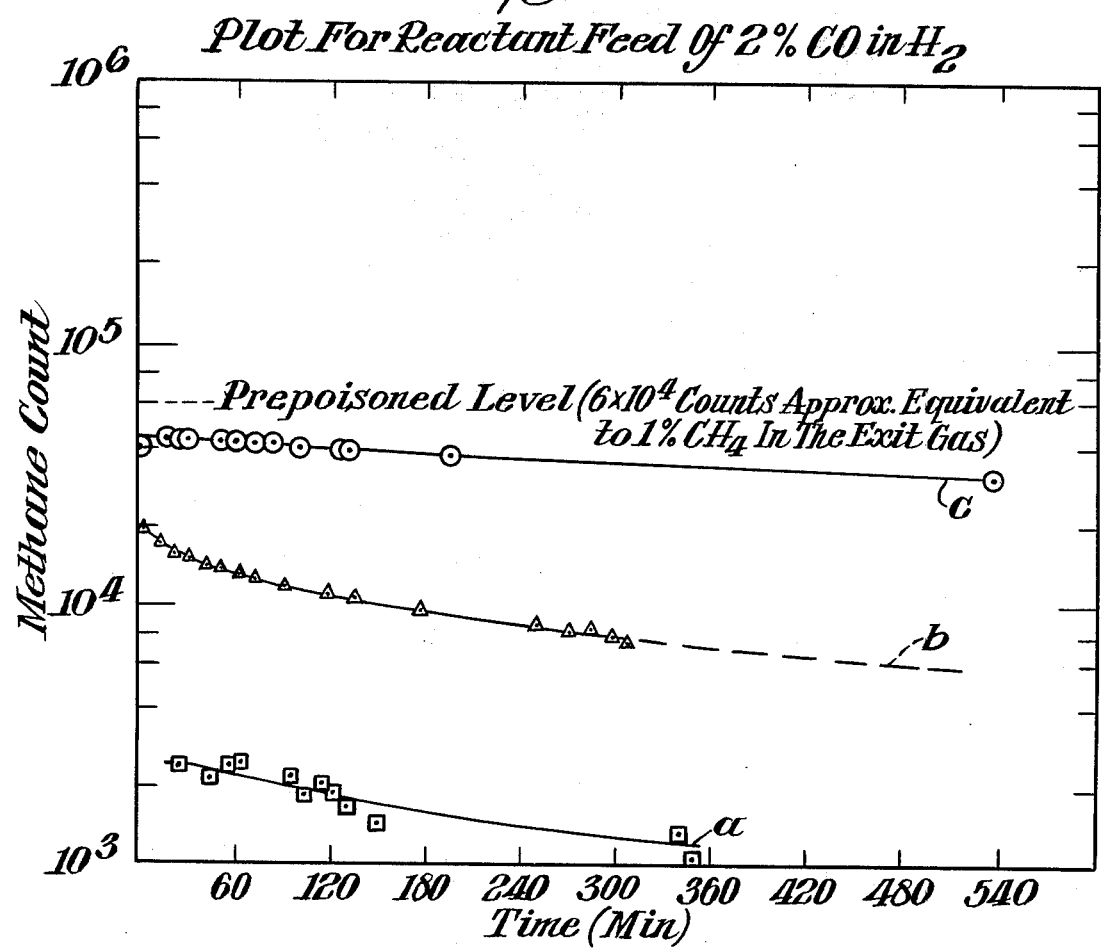
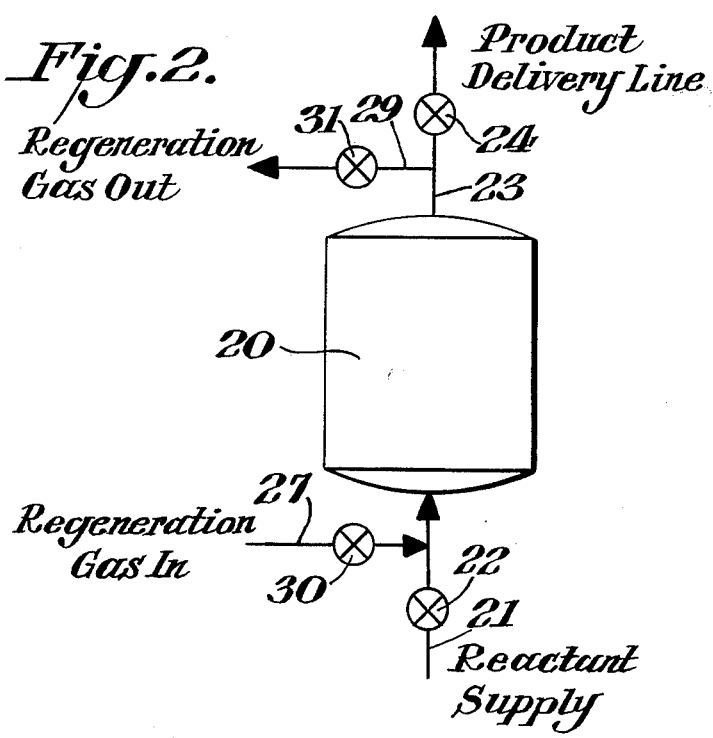

4,260,518

PROCESS FOR THE REGENERATION OF METALLIC CATALYSTS

BACKGROUND OF THE INVENTION

Metallic catalysts, particularly those supported on oxide carriers such as $ZrO_2$ and $Al_2O_3$, employed in reforming, hydrogenation and synthesis gas conversion are strongly deactivated by sulfur contained in the feed gas. Also, deactivation by carbon deposits can accompany sulfur deposition on the catalyst surface. The accumulation of sulfur and/or carbon on the catalyst surface leads to loss of catalytic activity (poisoning) so that either regeneration is required to reactivate the catalyst or there must be replacement of the poisoned catalyst with a fresh catalyst charge.

Hydrogenation metallic catalysts, particularly nickel, employed in the hydrogenation of carbon monoxide to methane, are especially susceptible to sulfur poisoning because of the apparent strong bonding of sulfur to nickel surfaces. Thus, at 400° C., dilute concentrations of only about 10 parts/billion of hydrogen sulfide in hydrogen can saturate the surface of nickel with a sulfur layer existing as a stable surface sulfide with accompanying complete destruction of catalytic activity within short time periods. This minute concentration of $H_2S$ in a hydrogen carrier has been found to deactivate severely catalysts employed in methanation and is indicative of the significantly higher stability of the surface sulfide (i.e., sulfur adsorbed on the surface) as compared with the nickel-molybdenum sulfide (i.e., the sulfide existing as bulk sulfide) in the nickel-molybdenum sulfide catalysts conventionally employed in commercial hydrodesulfurization or hydrodenitrogenation processes. Consequently, due to the exceptionally strong surface bonding of sulfur to metallic nickel, and to other metal catalysts such as rhodium, palladium, iridium, platinum and ruthenium, it has not hitherto been practicable to remove sulfur from such catalysts. Since synthesis gas conversion processes invariably utilize feed gases with hydrogen sulfide concentration levels substantially in excess of reported catalyst poisioning levels, a regeneration process is very much in demand.

Description of the invention

This invention comprises a process for complete regeneration of metal catalysts poisoned by sulfur and/or carbon. For methanation catalysts, the process necessitates no transfer or removal of catalyst from the reaction bed and is operable at temperatures near to, or lower than, those of the reaction process.

One specific catalyst selected for intensive investigation in the reduction to practice of this invention was metallic nickel supported on a refractory oxide carrier, e.g., $ZrO_2$ or $Al_2O_3$. The course of investigation was to first establish a steady-state catalytic activity for a given catalyst and, thereafter, expose the catalyst to sulfur in the form of $H_2S$ either during the methanation reaction or incident to $H_2S$ in a $H_2$ stream flow through. $H_2S$ in $H_2$ concentrations employed were in the general range of 1–10 ppm (parts per million.)

The activity of the catalyst was investigated after $H_2S$ exposure as described supra and invariably revealed that sulfur caused poisoning of the catalyst, as evidenced by substantially reduced methanation catalytic activity.

When deactivation was either complete, or alternatively carried to a preselected level, the feed of CO and then $H_2$ (as well as $H_2S$ contained in the latter) was halted and regeneration initiated with the poisoned catalyst in place and the general reaction temperature maintained at 320°–450° C.

Regeneration comprised contacting the poisoned catalyst with oxygen gas in a concentration of about 1–10 ppm. in either nitrogen, helium or flue gas, i.e., oxygen-depleted air. Regeneration was effected to substantial completion when the number of oxygen molecules passed through the poisoned catalyst bed was 10–20 times larger than the total number of hydrogen sulfide molecules supplied during the poisoning of the catalyst. At this point, the regeneration was halted and the activity of the catalyst was determined by passing sulfur-free CO in $H_2$ at pre-poisoning conditions. Complete regeneration of catalytic activity was either observed, or the regeneration treatment was repeated in order to obtain complete regeneration.

Poisoning and regeneration of specific catalysts were repeated in cyclic order, with the catalyst completely regenerated after each poisoning cycle.

The following drawings constitute part of this disclosure, in which:

FIG. 1 is a plot of methane count (wherein methane count is directly proportional to methane concentration in the reactor exit gas) on the ordinate v. time illustrative of the regeneration of methanation activity for a sulfur-poisoned metallic nickel catalyst deposited on a conventional $Al_2O_3$ carrier, with particular application to Example IV infra, and FIG. 2 is a schematic representation of a preferred equipment arrangement adapted to the industrial utilization of this invention.

The following testing activity is submitted in support of this invention.

EXAMPLE I

A metallic nickel catalyst supported on a $ZrO_2$ carrier was placed in a packed bed reactor, the catalyst consisting of 3.6 gms. total weight of 2.1 wt. percent Ni, 10–14 mesh. The catalyst bed was exposed to 5 ppm. $H_2S$ during a methanation reaction (5% CO in $H_2$, 60 cc./min. total flow rate at 285° C.) until the activity was reduced to 6% of pre-poisoned level.

The reaction was halted and 3 ppm. of $O_2$ in 15 cc./min. nitrogen and 45 cc./min. helium was passed through the catalyst bed maintained at 350° C. for 144 hours.

The catalytic activity was then investigated at pre-poisoning conditions, i.e., 50 cc./min. 5% CO in $H_2$ at 285° C., and was found to be at 8% of pre-poisoned level.

The reaction was halted and the regeneration was repeated for 240 hours at conditions identical with the first regeneration.

The catalytic activity was then appraised again at pre-poisoning conditions and was found to be restored but thereafter decreased to 21% in 20 hours.

The reaction was halted and the regeneration step was repeated for 192 hours. The catalytic activity was then appraised, and it was found that complete regeneration had beed achieved with stable activity level at pre-poisoned level.

EXAMPLE II

One gram of Ni on $ZrO_2$ carrier catalyst (2.1 wt. percent Ni loading, 10–14 mesh) was partially poisoned with sulfur by flowing 5 ppm. $H_2S$ in $H_2$ over the catalyst bed at 50 cc./min. and 310° C. After 7 hours, the $H_2S$ flow was discontinued and the catalyst activity was investigated at pre-poisoning conditions, i.e., 50 cc./min. flow rate of 5% CO in $H_2$, 310° C. The residual catalytic activity was found to be at 45% of pre-poisoned level. After 2.5 hours of reaction the activity dropped to 5% of the pre-poisoned level. The reaction was then halted and the temperature was raised to 400° C. in flowing S-free hydrogen. After 3 hours, $H_2$ flow was discontinued and regeneration was commenced with 8 ppm. $O_2$ in 20 cc./min. He admixed with 40 cc./min. $N_2$ flowed through the catalyst bed at 60 cc./min. total for 24 hours.

The catalyst activity was then investigated at pre-poisoning conditions, i.e., 5% CO in $H_2$ at 50 cc./min. flow rate at 310° C., and was found to be unregenerated.

Regeneration was then attempted with 7 ppm. $O_2$ in 35 cc./min. $N_2$ admixed with 25 cc./min. He flowed through the catalyst bed at a total flow of 60 cc./min. at 400° C. for 66 hours.

The catalyst activity was then investigated at pre-poisoning conditions and was found to be restored to the 56% pre-poisoned level.

The last regeneration step, i.e., 7 ppm. $O_2$ for 66 hours at 400° C. and 35 cc./min. $N_2$ plus 25 cc./min. He flow was repeated, after which the catalyst activity was retested and found to be improved to the 90% pre-poisoned level.

EXAMPLE III

One gram of metallic Ni catalyst deposited on a $ZrO_2$ carrier (2.1 wt. percent Ni loading on the 10–14 mesh carrier) was partially poisoned with sulfur by flowing 5 ppm. $H_2S$ in $H_2$ through the catalyst bed at 50 cc./min. and 310° C.

After 2.5 hours, the $H_2S$ flow was melted and the catalyst activity was investigated at pre-poisoning conditions, i.e., the combination of 5% CO with $H_2$ at a flow rate of 50 cc./min. at a temperature of 310° C. The residual catalyst activity was found to be reduced to 86% of pre-poisoned level.

After 80 minutes of continued catalyzed reaction of CO with $H_2$, the catalyst activity was found to drop further to 72% of pre-poisoned level. After an additional 17 hours of catalyzed reaction, the catalyst activity was found to have decreased to 28% of the pre-poisoned level, possibly as a result of carbon deactivation due to carbon deposition.

At this point, the catalyst was subjected to exposure to 5 ppm. of $H_2S$ in $H_2$ at a flow rate of 50 cc./min. and 310° C. for 3 hours, which dropped catalytic activity to 4% of the pre-poisoned level, when further exposure was halted.

After flushing the catalyst bed with sulfur-free hydrogen for 10 minutes, $H_2$ flow was discontinued and regeneration was commenced with 6 ppm. $O_2$ in 30 cc./min. $N_2$ admixed with 30 cc./min. He with the level temperature set at 400° C. After 70 hours, the catalyst activity was investigated at pre-poisoning conditions and found to be restored completely.

After the foregoing regeneration, the reaction was halted and the catalyst was partially poisoned by flowing 5 ppm. of $H_2S$ in $H_2$ through the catalyst bed at 50 cc./min. and 310° C. for 3 hours, after which catalyst activity was appraised at pre-poisoning conditions. The residual catalyst activity was found to be 82% of pre-poisoned level. The catalyst was then utilized to catalyze the reaction of 5% CO with $H_2$ for 17 hours, after which the catalyst activity was found to have fallen to 1% of pre-poisoned level, possibly due to carbon buildup.

The catalyst bed was then flushed with S-free hydrogen for one hour. Regeneration was thereupon attempted with 12 ppm. $O_2$ admixed with He flowed through the reaction bed at 50 cc./min. with the bed temperature maintained at 400° C. After 46 hours, catalyst activity was tested and found to be at 65% of the pre-poisoned level.

$CO/H_2$ flow was then halted and the catalyst was partially poisoned with sulfur by flowing 5 ppm. of $H_2S$ in $H_2$ through the catalyst bed maintained at 310° C. at a flow rate of 50 cc./min. After 3.5 hours, $H_2S$ exposure was discontinued and the catalytic activity tested at pre-poisoning conditions whereupon the residual activity was found to be 49% of the pre-poisoned level. The catalyst was then returned to $CO/H_2$ reaction service for 1.5 hours after which the catalyst activity fell to 30% of the pre-poisoned activity, possibly due to certain deactivation.

The reaction was halted and regeneration was again attempted with 12 ppm. $O_2$ in He was passed through the catalyst bed at 60 cc./min. with the temperature maintained at 400° C. After 63 hours the catalyst activity was tested and found to be at 47% of pre-poisoned level.

The foregoing regeneration treatment was repeated twice for 24 hour periods, after which the catalyst activity had a final test value of only 44% of pre-poisoned level. It is believed that at relatively high oxygen partial pressures existing at 12 ppm. and higher $O_2$ concentration, the metallic nickel possibly oxidizes and then overlies adsorbed sulfur instead of removing it.

In view of the lack of success of regeneration with 12 ppm. $O_2$ concentration, an attempt was made to regenerate the same catalyst sample with 8 ppm. $O_2$ in He supplied at a flow rate of 60 cc./min. for 24 hours at a bed temperature of 400° C., which restored catalyst activity to 56% of the pre-poisoned level.

Further regeneration with 7 ppm. $O_2$ in He at a flow rate of 60 cc./min., temperature 400° C. for a time period of 24 hours resulted in complete restoration of catalyst activity.

EXAMPLE IV

One gram of metallic Ni catalyst deposited on an $Al_2O_3$ carrier (supplied by the Harshaw Chemical Company and analyzing 11 weight percent Ni on a 10–14 mesh $Al_2O_3$ carrier) was exposed to one ppm. $H_2S$ at a flow rate of 40–60 cc./min., bed temperature 350° C., with the catalyst disposed in a glass flow reactor for 30 days. The $H_2S$ supply was then halted and the catalyst activity investigated at 330° C. by passing a mixture of 2% CO in $H_2$ through the catalyst bed at a flow rate of 40 cc./min. The catalyst methanation activity was found to be zero, i.e., no methane was selected by gas chromatography.

The $CO/H_2$ flow was halted and regeneration was attempted with one ppm. $O_2$ in He at a flow rate of 46 cc./min. for 72 hours with the bed temperature maintained at 350° C. The catalyst activity was then investigated with $CO/H_2$ at pre-poisoning conditions. The catalyst activity was found to have been regenerated to about 4% of the pre-poisoned level, as shown by curve a, FIG. 1.

CO/H$_2$ supply was then halted and renewed regeneration was attempted by supply of 1.2 ppm. O$_2$ in He for 264 hours. The catalyst activity was then pre-appraised at the identical conditions utilized in the obtainment of curve a, which revealed an increase of catalyst activity to about the 30% pre-poisoned level, as shown by curve b, FIG. 1.

CO/H$_2$ supply was then halted and further regeneration was attempted with 1.8 ppm. O$_2$ in He at a flow rate of 40 cc./min. and a temperature of 350° C. over 264 hours. The catalyst activity was then appraised at the identical condtions reported supra, which revealed a methane count of 80% pre-poisoned level, as shown by curve c, FIG. 1.

EXAMPLE V

A fresh 0.2 gm. sample of the identical Ni/Al$_2$O$_3$ catalyst utilized in Example IV was exposed to 5 ppm. H$_2$S in mixture with 5% CO, remainder H$_2$, at a flow rate of 80 cc./min. and a catalyst bed temperature of 300° C.

Within 11 hours the catalyst activity fell to 20% of pre-poisoned level.

The flow of H$_2$S and CO was then halted; however, hydrogen supply was continued through the hot catalyst bed for 2 hours while the temperature was raised to 350° C., which elevation took 30 minutes to achieve.

H$_2$ flow was then halted and 3 ppm. O$_2$ in 20 cc./min. N$_2$ plus 60 cc./min. He was passed through the reactor bed, the temperature of which was maintained at 350° C.

After 144 hours, regeneration was discontinued and S-free hydrogen was passed through the reactor bed for 30 minutes. The catalyst activity was then tested and found to be at 60% of the pre-poisoned level.

Referring to FIG. 2, the regeneration process of this invention can be readily utilized in conjunction with already installed apparatus for methanation or other catalyzed reactions.

Thus, if vessel 20 is the conventional methanation reactor, heated to predetermined temperature by means not detailed, where reactants are supplied via line 21 provided with valve 22 and product is delivered via line 23 provided with valve 24, the only modifications required are the additions of valved regeneration gas input line 27 and regeneration gas exhault line 29. Then, when regeneration is required, reactant valves 22 and 24 are closed and regeneration valves 30 and 31 opened for the duration of the regeneration operation. In some instances, it may be advantageous to introduce regeneration gas from top to bottom of reactor 20, in which case the directions of regeneration gas supply and discharge are simply reversed over those shown in FIG. 2. If it is desired to manufacture product continuously, a duplicate apparatus exactly like that shown in FIG. 2 is connected in parallel therewith, so that one reactant vessel 20 can always be retained in service while its companion is undergoing regeneration.

While the invention has been described with particular reference to metallic Ni as catalyst, it will be understood that it is equally useful for the regeneration of other metallic catalysts including Rh, Pd, Ir, Pt and Ru poisoned with sulfur with or without accompanying carbon deposition.

Also, inert gases suitable for regeneration oxygen dilution include argon, xenon and krypton as well as helium, nitrogen and flue gas, i.e., air substantially free of oxygen.

Finally, regeneration according to this invention is preferably conducted in the general atmospheric pressure range.

What is claimed is:

1. A method for the regeneration of a metallic hydrogenation catalyst which had been used as a methanation catalyst for the reaction of CO with H$_2$ from the class consisting of Ni, Rh, Pd, Ir, Pt and Ru poisoned with sulfur, with or without accompanying carbon deposition, comprising subjecting said catalyst to exposure to oxygen gas in a concentration of about 1–10 ppm. intermixed with an inert gas of the group He, A, Xe, Kr, N$_2$ and air substantially free of oxygen to an extent such that the total oxygen molecule throughout is in the range of about 10 to 20 times that of the hydrogen sulfide molecular exposure producing the catalyst poisoning while maintaining the temperature in the range of about 300° to 500° C. until said regeneration is completed.

2. The method of claim 1 wherein the gas pressure is maintained in the general atmospheric pressure range.

3. The method of claim 1 wherein said metallic catalyst to be regenerated is supported on an oxide carrier.

4. The method of claim 3 wherein said oxide carrier is one of the group consisting of ZrO$_2$ and Al$_2$O$_3$.

* * * * *